United States Patent [19]
Heiman

[11] Patent Number: 6,153,559
[45] Date of Patent: *Nov. 28, 2000

[54] N-ACETYL AVG AND ITS USE AS AN ETHYLENE BIOSYNTHESIS INHIBITOR

[75] Inventor: Daniel F. Heiman, Libertyville, Ill.

[73] Assignee: Valent BioSciences, Inc., Libertyville, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/927,941

[22] Filed: Sep. 11, 1997

Related U.S. Application Data

[63] Continuation-in-part of application No. 08/717,785, Sep. 23, 1996, abandoned.

[51] Int. Cl.$^7$ ..................................................... A01N 3/02
[52] U.S. Cl. ..................... 504/115; 504/147; 504/302; 560/169; 562/564
[58] Field of Search ............................ 562/564; 504/115, 504/147, 320; 560/169

[56] References Cited

U.S. PATENT DOCUMENTS

| | | |
|---|---|---|
| 3,751,459 | 8/1973 | Berger et al. . |
| 3,775,255 | 11/1973 | Berger et al. . |
| 3,887,615 | 6/1975 | Keith et al. . |
| 4,014,898 | 3/1977 | Keith et al. . |
| 4,115,105 | 9/1978 | Scannell et al. . |
| 4,216,008 | 8/1980 | Weigele et al. . |
| 4,238,622 | 12/1980 | Keith ......................................... 560/39 |
| 4,372,776 | 2/1983 | Day et al. . |
| 4,457,870 | 7/1984 | Schröder et al. . |
| 4,494,982 | 1/1985 | Schröder et al. . |
| 5,284,818 | 2/1994 | Shafer et al. . |
| 5,500,403 | 3/1996 | Shafer et al. . |

FOREIGN PATENT DOCUMENTS 1042460 11/1978 Canada .

OTHER PUBLICATIONS

Matte, HortScience, vol. 14, pp. 503–504, 1979.
Dekazos, E. D., "Effects of Aminoethoxyvinylglycine (AVG) on Bloom Delay, Fruit Maturity and Qualilty of 'Triblue' and 'Woodward' Rabbiteye Blueberries" *Proc. Fla.Stat Hort. Soc.,* 92:248–252 (1979).
Natti, T.A., "Role of Wound Ethylene in Fruit Set of Hand–pollinated Muskmelons", *J. Amer. Soc. Hort. Sci.,* 103(6):834–836 (1978).
Keith, D. D., et al., "Synthesis of DL–2–Amino–4–(2–aminoethoxy)–trans–but–3–enoic Acid", *J. Org. Chem.,* 43(19):3713–3716 (1978).

*Primary Examiner*—Michael L. Shippen
*Attorney, Agent, or Firm*—Rockey, Milnamow & Katz, Ltd.

[57] ABSTRACT

A compound, compound I, is disclosed which inhibits ethylene production in plants. In addition, aqueous formulations comprising compound I are disclosed as well as methods of applying formulations comprising compound I to plants.

18 Claims, 1 Drawing Sheet

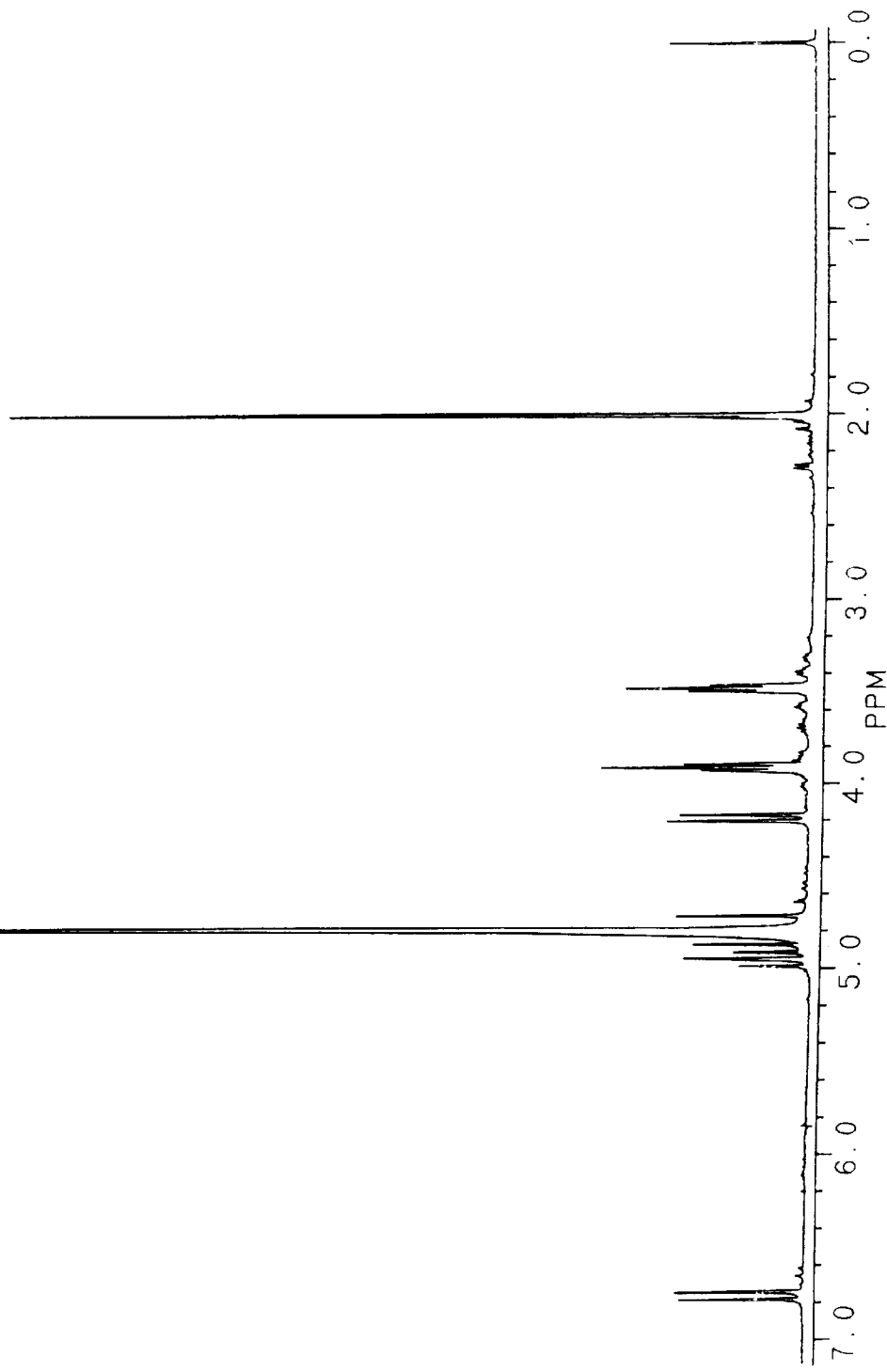

N-ACETYL AVG AND ITS USE AS AN ETHYLENE BIOSYNTHESIS INHIBITOR

This is a continuation-in-part of U.S. Ser. No. 08/717,785 filed Sep. 23, 1996, now abandoned.

FIELD OF THE INVENTION

This invention relates to the discovery of a new chemical compound, L-trans-2-amino-4-(2-acetamidoethoxy)-3-butenoic acid (N-acetyl AVG), and processes for preparing it. The compound may be prepared by chemical synthesis from L-trans-2-amino-4-(2-aminoethoxy)-3-butenoic acid (AVG) or as a biosynthetic transformation product in plants from the same precursor.

BACKGROUND OF THE INVENTION

It has been known for some time that plants produce ethylene by converting methionine through S-adenosylmethionine into 1-aminocyclopropane-1-carboxylic acid (ACC) which is then broken down into ethylene, HCN and carbon dioxide. The plant enzyme responsible for the production of ACC is called ACC synthase. Ethylene, a gaseous phytohormone, is believed to be involved in the modulation of a number of plant biochemical pathways affecting such processes as abscission, senescence, flowering, fruit setting, fruit ripening, seed germination, sex expression, root growth, internode elongation, epinasty, and geotropism.

The marketing of cut flowers and ornamental flowering plants is of considerable economic importance to the horticultural industry. The total wholesale market for cut flowers, flowering plants and foliage and bedding plants in 1994 was approximately 1.3 billion dollars. The sale of cut flowers contributed approximately 15% to this total, and the sale of potted flowering plants contributed approximately 23%. The marketing of these products generally involves shipping from the site where the flowers are grown to commercially important markets elsewhere in the country. The handling, packaging and shipping of both cut flowers and ornamental plants places stresses upon them which can result in damage, diminishing their commercial value to the retailer. The stresses placed on plants result in early senescence (aging and browning) which can be due, in part, to the effects of ethylene. Ethylene gas, either produced by the plant itself in response to stress or in the environment causes acceleration of senescence. Plants which look good at harvest with burgeoning flowering buds can look unhealthy and lose many of their buds after transport.

A number of chemicals which limit ethylene-induced damage to cut flowers have been identified. These include silver thiosulfate, 1-methylcyclopropene (MCP) (cf. *Plant Growth Regulation,* vol. 18, pp. 169–174 (1996), carboxymethoxylamine (also known as aminooxyacetic acid (AOAA)), AVG, rhizobitoxine, and L-trans-2-amino-4-methoxy-3-butenoic acid (MVG). Silver thiosulfate and MCP are believed to inhibit the effect of either internal or external ethylene, while the others are believed to act internally to inhibit the ability of the cut flowers, plants, and fruit to produce ethylene. These compounds (except MCP) are typically applied to plants or plant materials in the form of an aqueous treatment solution. Applications of the treatment solution to potted plants are carried out by spraying it onto the aerial parts of the plants or by including it in the irrigation water which is supplied to their roots. Treatment of cut flowers or greens is typically carried out by immersing the cut ends of the stems in the aqueous solution containing the treating agent immediately after harvest, during transportation or while the floral arrangement is on display, although they might be treated by immersing the whole flowers into a solution or by spraying them. Since MCP is a gas, it cannot readily be applied in aqueous solution, so plants are treated by exposing them to a modified, controlled atmosphere (containing a defined amount of MCP) in an enclosed chamber.

Silver thiosulfate is expensive and cannot be applied to large-acreage, low value crops economically. In addition, it may be toxic to animals, including humans, and for that reason cannot be applied to food or food crops. MCP has not been widely used because of difficulties in production and application and its lack of stability.

The role of ethylene in the ripening of fruit has been recognized in the art for over 40 years. It is known that the rate of production of ethylene in maturing fruit increases while the fruit separates from its pedicel through the formation of a layer of cells with low adhesion known as the abscission layer. If the formation of this layer is completed before the fruit can be picked, the fruit falls to the ground, sustaining injury, which results in a poorer quality. Thus, the prevention of preharvest fruit drop is of significant economic benefit to the grower. In addition, fruit typically has a higher resistance to bruising and penetration injury before or immediately after harvest than after storage for a period of time. The resistance of fruit to penetration is measured with a device called a penetrometer and is reported as fruit firmness. Fruit firmness is also a generally accepted measure of crispness and freshness. Typically at harvest, fruit has a higher fruit firmness than after storage. It is thought that the decrease in fruit firmness over time is, at least indirectly, related to production of ethylene within the fruit.

AVG is a plant growth regulator which inhibits ethylene production. It acts by inhibiting the plant enzyme ACC synthase. However effective AVG is at inhibiting ethylene biosynthesis, there continues to be a need for identifying additional inhibitors of ethylene biosynthesis.

BRIEF DESCRIPTION OF THE DRAWINGS

FIG. 1 depicts the proton NMR of L-trans-2-amino-4-(2-acetamidoethoxy)-3-butenoic acid (N-acetyl AVG).

SUMMARY OF THE INVENTION

The present invention provides the novel compound, L-trans-2-amino-4-(2-acetamidoethoxy)-3-butenoic acid (N-acetyl AVG)

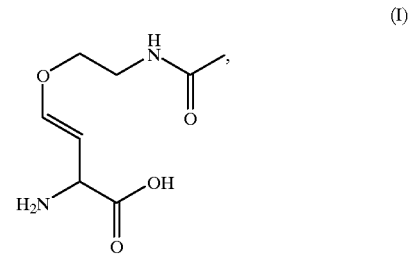

(I)

or a salt thereof.

The present invention also provides for processes and formulations for inhibiting ethylene biosynthesis comprising N-acetyl-AVG.

DETAILED DESCRIPTION OF THE INVENTION

Ethylene is a natural hormone in plants. AVG is an agent that inhibits ethylene biosynthesis in plants, and as such may be used to retard aging and alter stress-response processes of cut flowers and fruit crops. AVG also improves the storageability of plants, fruit, vegetables and cut flowers. A novel finding of the present invention is the terminal acetamide of AVG (N-acetyl-AVG), a synthetic or biotransformation product derived from AVG. Following exogenous application of AVG, the concentration of N-acetyl-AVG increases in plants as AVG concentrations decrease due to AVG bioconversion.

The present invention discloses the novel compound, N-acetyl AVG, shown as compound (I)

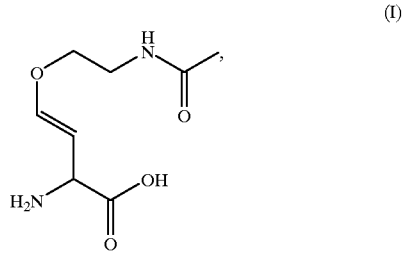

(I)

or an ester, prodrug, or salt thereof.

N-acetyl AVG or an ester, prodrug, or salt thereof can be applied in formulations to plants to inhibit ethylene biosynthesis. In addition, AVG formulations may be applied to plants wherein N-acetyl AVG may inhibit ethylene biosynthesis as bioconversion of AVG to N-acetyl AVG occurs.

The term "formulations" as used herein includes (i) AVG formulations comprising AVG or an ester, prodrug, or salt thereof where bioconversion in vivo of AVG or the ester, prodrug, or salt of AVG to N-acetyl AVG or an ester, prodrug, or salt of N-acetyl AVG occurs in plants, or (ii) formulations comprising N-acetyl AVG or an ester, prodrug, or salt thereof, or (iii) AVG/N-acetyl AVG mixture formulations or esters, prodrugs, or salts thereof.

It is believed that the acetamide of N-acetyl AVG inhibits ethylene biosynthesis due to the presence of an alpha-amino and beta-olefinic functional group of the acetamide, two requirements for competitively inhibiting the enzyme ACC synthase.

The term "plant(s)" as used herein refers to green, terrestrial plants. Green, terrestrial plants include, but are not intended to be limited to, field-grown plants including fiber plants and food plants, forestry plants, lawn grasses, foliage plants and ornamental plants. Food plants include, but are not intended to be limited to, vegetable plants, grain plants, and fruit plants. Vegetable plants may include, but are not intended to be limited to, bean, corn, potato, tomato, broccoli, soybean, squash, cucumber, lettuce, and onion. Grains plants may include, but are not intended to be limited to, oats, rice, wheat, and barley. Fiber plants may include, but are not intended to be limited to cotton and flax. In addition, the formulations of the present invention may also be used to treat cut decorative greens and cut ornamental flowers.

The formulations of the present invention may be used on plants to inhibit ethylene biosynthesis. The formulations of the present invention may be used in pre- and/or postharvest application where harvesting is relevant.

The present invention also discloses the novel compound (I) as a senescence inhibitor in plants and the use of compound (I) in formulations for application to plants. For example, formulations comprising N-acetyl-AVG may be used to inhibit ethylene biosynthesis in -plants.

Compound (I) of the present invention may be used in the form of salts derived from inorganic or organic acids. The salts can be prepared in situ during the final isolation and purification of the compound of the present invention, or separately by reacting the free base function with a suitable organic acid. These salts include but are not limited to the following: acetate, citrate, aspartate, benzoate, benzenesulfonate, bisulfate, butyrate, heptanoate, hexanoate, fumarate, hydrochloride, hydrobromide, hydroiodide, lactate, maleate, methanesulfonate, oxalate, propionate, succinate, tartate, and thiocyanate.

Examples of acids which may be employed to form acceptable salts of the compound of the present invention include such inorganic acids as hydrochloric, sulphuric, and phosphoric acids and such organic acids as acetic, oxalic, maleic, succinic, and citric acids.

Basic addition salts can be prepared in situ during the final isolation and purification of the compounds of formula (I), or separately by reacting the carboxylic acid function of compound (I) with a suitable base such as hydroxide, carbonate or bicarbonate of a metal cation or with ammonia, or an organic primary, secondary or tertiary amine. Salts of the present invention include, but are not limited to, cations based on the alkali and alkaline earth metals such as sodium, lithium, potassium, calcium, magnesium, aluminum salts and the like. It is well known to one skilled in the art on how to prepare salts of compound (I).

The term "ester" as used herein refers to esters which hydrolyze in vivo and include those that break down in a plant to leave the parent compound or a salt thereof. Suitable esters include, for example, those derived from acceptable aliphatic and aromatic alcohols, particularly staight or branced chain alkyl and alkenyl alcohols and benzylic, in which each alkyl or alkenyl moiety advantageously has not more than 6 carbon atoms. Examples of particular esters include, but are not limited to, methyl, ethyl, ethenyl, propyl, propenyl, isopropyl, isopropenyl, butyl, benzyl, and butenyl esters.

The term "prodrug" as used herein refers to those derivatives of the compounds of the present invention which are suitable for use in contact with the plant. The term "prodrug" refers to compounds that are rapidly transformed in vivo to provide the parent compound having formula I. A thorough discussion is provided in T. Higuchi and V. Stella, *Pro-drugs as Novel Delivery Systems,* Vol. 14 of the A.C.S. Symposium Series, and in Edward B. Roche, ed., *Bioreversible Carriers in Drug Design,* American Pharmaceutical Association and Pergamon Press, 1987, both of which are incorporated herein by reference.

In one embodiment of the present invention, Compound (I) may be used in formulations for single or multiple applications to plants. Moreover, AVG may be used as the starting material for application to plants. As AVG biotransformation occurs over time, N-acetyl AVG becomes an increasingly important ethylene biosynthesis inhibitor.

In another embodiment of the present invention, a combination of AVG and N-acetyl AVG may be used in the formulations of the present invention.

The formulations of the present invention are not limited, however, to use in protecting potted flowering ornamental plants from shipping damage. The formulations of the present invention may be applied to food plants. Food plants include, but are not intended to be limited to, vegetable plants, grain plants, and fruit plants. The formulations of the present invention may be applied to food plants plants pre or post harvest or both. The formulations may be applied to fruited plants including, but not intended to be limited to, pome fruit, stone fruit, berry, grape, and tomato. Examples of pome fruit wherein the formulations of the present invention may be useful include, but are not intended to be limited to, apples and pears. Examples of stone fruit wherein the formulations of the present invention may be useful include, but are not intended to be limited to, peach, cherry, apricot, olive, plum, nectarine, prune, and almond. N-acetyl-AVG formulations may be used to improve the quality of crops by means of pre- and/or post-harvest applications. They may also help prevent premature drop of the fruit from the tree when applied pre-harvest. This can be an economic benefit to the grower because fruit that drops from trees usually becomes bruised and can only be sold at a fraction of the unbruised fruit cost.

The formulations of the present invention may be applied to fiber plants as well. Examples of fiber plants include, but are not intended to be limited to, cotton and flax.

The formulations of the present invention may also allow spraying of plants at an earlier time than is usual with other products. For example, it may be possible to spray apple trees 5 to 6 weeks prior to harvest rather than at 2 to 4 weeks prior to harvest. This provides advantages in that it gives the grower greater flexibility in the timing of application and may allow for a combined spraying with some other treatment required for managing the crop, e.g., insecticidal spraying.

The formulations of the present invention are generally applied to growing plants by either spraying the foliage, buds, fruit, and flowers or by soil drench. When applied by spraying, the formulations are sprayed onto the aerial parts of the plant, preferably to the point of runoff, by techniques well known to the art. In this method it is preferred, although not necessarily required, that the formulations contain a non-ionic surfactant to thoroughly wet the foliage and buds, flowers and/or fruits with the formulations.

In the soil drench method, the formulation may be poured into the soil surrounding the plant or can be applied to the roots from below as, for example, in the technique known as "ebb-and-flow" where water and nutrients are applied to growing plants on a greenhouse bench from below. In these techniques, a surfactant is typically not included in the formulation.

In one embodiment of the present invention, flower senescence of potted ornamental plants during shipping may be prevented. Current practice in the industry is to "sleeve" or "box" commercial potted plants, pack them into shipping cartons, and surface ship the sleeved and boxed plants in refrigerated trucks or rail cars to their destination. While cut flowers are often air-shipped, surface shipment is often the only commercially feasible means for shipping potted plants because of the additional weight of the pot and soil. Some commercial flowering plants such as miniature carnations (Dianthus sp.) which are grown on the East and West coasts of the United States are not widely sold because the damage to the plants caused by the stresses of shipment which ultimately destroy the commercial value of the plants at the destination. The formulations of the present invention comprising compound (I) provide a means of protecting such plants from premature senescence.

The formulations of the present invention may alternatively be applied to fruits or vegetables after harvest by either spraying the fruits or vegetables with a solution containing N-acetyl AVG or by dipping or immersing the fruits or vegetables into the solution for a period of time.

The formulations of the present invention may contain adjuvants such as preservatives, wetting agents, emulsifying agent, and dispersing agents.

Formulations of the present invention comprising AVG or N-acetyl-AVG or the esters, prodrugs, or salts thereof, may be present in a liquid medium in concentrations ranging between about 10 parts per million (ppm) and 2000 parts per million (ppm), with concentrations near the lower end of this range being preferred when the formulations of the present invention are applied to plants by the soil drench method. When the formulations are applied to plants by spray techniques, concentrations ranging between about 50–1000 ppm are preferred. The formulations may also include a non-ionic surfactant, particularly if the intended use involves spray application of the formulations to the plants. The liquid medium is preferably aqueous, but may include or consist essentially of an organic solvent wherein N-acetyl AVG and/or AVG are soluble. In the case where an organic solvent is used, the solvent should not be detrimental to the plants. U.S. Pat. No. 5,500,403 and U.S. Pat. No. 5,523,281 describe AVG formulations and methods of using such formulations and are hereby incorporated entirely by reference.

Formulations comprising AVG or an ester, prodrug, or salt thereof may be applied to plants wherein bioconversion of AVG or an ester, prodrug, or salt thereof to N-acetyl AVG or an ester, prodrug, or salt thereof occurs in vivo.

The N-acetyl formulations are typically prepared by dissolving N-acetyl-AVG in a liquid medium, preferably water, and adding the surfactant (if needed), and finally diluting the mixture to the desired application concentration.

The following examples are representative of the present invention, but are not intended to be fully definitive or limiting.

EXAMPLE 1

Synthesis of N-acetyl-AVG

The synthesis of N-acetyl AVG was carried out using copper chelation to prevent reaction at the alpha-amino group of AVG.

L-trans-2-amino-4-(2-aminoethoxy)-3-butenoic acid (AVG) (1.97 g, 10 mmol, 1 eq, Abbott Laboratories, North Chicago, Ill.) was dissolved in 10 milliliters (mL) of deionized water, and 3.35 mL of 6 molar (M) aqueous sodium hydroxide (20 millimoles, 2 equivalents (eq)) was added. To this was added, dropwise with good stirring at ambient temperature, a solution of copper sulfate pentahydrate (1.273 g, 5.1 mmol, 0.51 eq) in 3 mL of water. The copper initially precipitated, but then rapidly redissolved to give an intensely blue solution. The mixture was stirred for one hour after addition of the copper solution.

Neat acetic anhydride (943 microliters ($\mu$L), 10 mmol, 1 eq) was added dropwise over a period of approximately one minute. This mixture was stirred for thirty minutes before storing at 4° C. overnight.

After rewarming to room temperature, 0.1 eq of sodium hydroxide solution (1.0 mL of 1.0 M, 1.0 mmol) was added, followed by another 0.1 eq of acetic anhydride (94 $\mu$L, 1.0 mmol), and stirring was continued for one hour. To remove the copper, the pH was adjusted to 8.0 with dilute sodium hydroxide solution, and thioacetamide (1.127 g, 15 mmol, 1.5 eq) was added. The mixture was allowed to stir at ambient temperature overnight. The abundant, finely-divided black precipitate was removed by filtration through a bed of diatomaceous earth (Celite®, Aldrich Chemical Company, Inc., Milwaukee, Wis.), the pH was adjusted to 6.5, and the solution was subjected to ion-exchange chromatography on a column of Dowex 50-X8-400 (Dow Chemical Company, Midland, Mich.) in the H$^+$ form (about 75 mL bed volume). After loading the reaction mixture onto the column, it was eluted with 175 mL of water (until the effluent was colorless), followed by 200 mL of 2% pyridine in water. The fractions containing the desired product were lyophilized to give 1.266 grams of tan to light yellow solid (63% of theoretical). The material gave the correct molecular ions of 203 for (M+H)$^+$ in the positive FAB mode and 201 for (M−H)$^−$ in the negative FAB mode. The carbon-13 NMR spectrum showed the expected signals at 24.67 (acetate methyl), 41.49 (terminal carbon of AVG), 56.88 (alpha carbon), 70.96 (ether methylene), 100.73 (vinyl adjacent to the alpha carbon), 155.78 (ether vinyl) and 176.65 and 177.14 ppm (carbonyl carbons). The proton NMR was also consistent with the proposed structure (FIG. 1). The melting point of N-acetyl-AVG was 178° C. with decomposition.

EXAMPLE 2

Biosynthesis of N-Acetyl-AVG in Apple Fruit

L-trans-2-amino-4-(2-aminoethoxy)-3-butenoic acid (AVG) labeled with carbon-14 at the alpha-carbon (Abbott Laboratories, North Chicago, Ill.) was dissolved in water at a concentration of 144.3 g/L or 532 mCi/L. This solution was applied to apple fruits (*Malus domestica* Borkh., cv. Gordon) 28 days before the fruit was expected to be fully ripe. Apples were harvested for analysis of radioactive residues on Day 0 (the date of application), Day 7, Day 14, and Day 28. The harvested apples were rinsed twice by immersion in distilled water (100–500 mL/rinse) to remove any radioactive material that remained on their surfaces. The rinses were combined and total radioactivity in the rinse was measured with a liquid scintillation counter (LSC).

Each apple was peeled and the peel and pulp were analyzed separately for radioactivity. The tissue (pulp or peel) was chopped into small pieces and frozen in liquid nitrogen, transferred to a blender and homogenized to a powder. Total radioactivity for peel and pulp samples were measured by LSC after combustion of an homogenized aliquot.

The rinse samples were also analyzed for AVG and N-acetyl AVG components by reverse-phase HPLC. To look at individual components in the peel and pulp samples, aqueous extracts were prepared by adding a five-fold amount of distilled water to a weighed aliquot of the powdered tissue and shaking vigorously for 30 min., followed by centrifugation. The aqueous extraction procedure was repeated, and the combined supernatants were subjected to analysis by reverse-phase HPLC. The chromatographic analysis in two different systems showed, for peel and pulp samples at all dates beyond Day 0, in addition to the peak which coeluted with unchanged L-trans-2-amino-4-(2-aminoethoxy)-3-butenoic acid, a radiolabeled peak which coeluted with an authentic sample of L-trans-2-amino-4-(2-acetamidoethoxy)-3-butenoic acid prepared in EXAMPLE 1. For confirmation of the structure of the product, a portion of an aqueous extract of the pulp of Day 21 apples was buffered to pH 3.4 and loaded onto SCX Bond-Elut SPE cartridges (Varian), washed with phosphate buffer and eluted with 0.5 M aqueous ammonia. The eluted material was concentrated to a small volume and injected repeatedly onto a preparative HPLC system (C18 column). The pooled fractions containing the labeled product were loaded onto Mega Bond Elut silica gel cartridges (Varian), washed with acetonitrile/water and eluted. The concentrated product was again subjected to preparative HPLC on a Selectosil SCX-110A column (Phenomenex) with an ammonium acetate buffer gradient. The pooled fractions containing the radioactive product gave LC/MS and proton nuclear magnetic resonance spectra identical to those produced by an authentic sample of L-trans-2-amino-4-(2-acetamidoethoxy)-3-butenoic acid prepared in EXAMPLE 1.

Table 1 shows the respective concentrations of AVG and N-acetyl AVG, expressed as percent of total recovered radioactivity, measured in each apple fraction harvested on Day 0, 7, 14, and 28.

TABLE 1

| | AVG | | | N-acetyl AVG | | |
|---|---|---|---|---|---|---|
| Day | Rinse | Peel | Pulp | Rinse | Peel | Pulp |
| 0 | 100 | 0 | 0 | — | — | — |
| 7 | 50.94 | 1.02 | 1.75 | 0 | 2.50 | 6.33 |
| 14 | 50.17 | 0.57 | 1.28 | 0 | 1.61 | 8.95 |
| 28 | 28.65 | 0.42 | 1.20 | 0 | 1.63 | 13.22 |

EXAMPLE 3

Mung-Bean Bioassay

Mung-bean seeds (*Vigna radiata*) were planted in plastic trays with a soilless bark mixture and grown in the dark at 25° C. under a relative humidity of greater than 90%. After 4 days, ten hypocotyl segments (2 centimeters (cm) in length) were excised from these etiolated seedlings and placed into 25 milliliter (ml) flasks. Five replicate flasks were used for each treatment. Each flask contained 9 ml of a indoleacetic acid (IAA) treatment solution, a known promoter of ethylene biosynthesis, with or without an inhibitor. Each flask was sealed with a rubber septum and incubated for 25 hours at 25° C. in the dark. Headspace gas was sampled from each flask and ethylene content determined on a gas chromatograph (Hewlett-Packard Model No. 5890) equipped with a FID (Flame Ionization Detector). Table 2 provides the final ethylene concentration measurements in parts per million of ethylene produced per ten segments per hour. The results show that 100 $\mu$M N-acetyl AVG produced a statistically significant (p=0.05) decrease in ethylene biosynthesis.

TABLE 2

| | Sample | Replicate 1 | Replicate 2 | Replicate 3 | Replicate 4 | Replicate 5 | Mean | Duncan Test* |
|---|---|---|---|---|---|---|---|---|
| A. | 100 $\mu$M IAA (control) | 0.271 | 0.277 | 0.259 | 0.272 | 0.220 | 0.260 | a |
| B. | 100 $\mu$M IAA + 10 $\mu$M N-Acetyl-AVG | 0.246 | 0.153 | 0.227 | 0.257 | 0.256 | 0.228 | a |

TABLE 2-continued

| | Sample | Replicate 1 | Replicate 2 | Replicate 3 | Replicate 4 | Replicate 5 | Mean | Duncan Test* |
|---|---|---|---|---|---|---|---|---|
| C. | 100 µM IAA + 100 µM N-Acetyl-AVG | 0.057 | 0.052 | 0.064 | 0.067 | 0.053 | 0.059 | b |
| D. | 100 µM IAA + 10 µM AVG | 0.007 | 0.012 | NA | 0.028 | 0.009 | 0.014 | c |
| E. | 100 µM IAA + 100 µM AVG | 0.003 | 0.000 | 0.000 | 0.000 | 0.000 | 0.001 | c |

*The data in Tables 2, 3 and 5 were statistically analyzed using the Duncan Multiple Range Test (Biometrics, 11:1–42 (1955). This procedure permits the carrying out of comparisons among a number of means or averages in a given set of data and is a widely used method of statistically analyzing data in biological experiments. The results are reported by using a letter designation (i.e., "a" or "b" etc.). Two valuesdesignated by the same letter are not statistically significantly different from one another while two values having different letter designations are statistically significantly different.

EXAMPLE 4

Cotton Cotyledon Bioassay

Cotton (*Gossypium hirsutum*) cultivar DP50 was planted in 3 inch cells with a soiless bark mixture and grown for 10–12 days in a growth chamber at 25° C. with alternating 18 hours of light and 6 hours of darkness. A 710 micromolar solution of 6-anilinopurine, a promoter of ethylene biosynthesis, with 0.1% organosilicone surfactant was sprayed onto the abaxial side of intact cotyledons of each plant and allowed to dry. The control plants had only 6-anilinopurine applied to them. Treated plants (cotyledons) had either AVG or N-acetyl AVG applied to the adaxial side. Plants were returned to the growth chamber for 48 hours at 25° C. with alternating 18 hours of light and 6 hours of darkness. Pairs of cotyledons were excised, weighed and then placed into 50 ml centrifuge tubes containing 1 ml water. Each tube was sealed with a rubber septum and incubated for 4–5 hours at 25° C. in the dark. Eight replicate tubes were used for each treatment. Headspace gas was sampled from each tube and ethylene content determined on a gas chromatograph (Hewlett-Packard Model No. 5890) equipped with a FID. Table 3 provides the final ethylene concentration measurements in parts per million of ethylene produced per gram weight of cotyledon per hour. The results show that N-acetyl AVG inhibits ethylene production.

TABLE 3

| Replicate | Control | 200 ppm N-Acetyl-AVG | 200 ppm AVG |
|---|---|---|---|
| | [Ethylene] | [Ethylene] | [Ethylene] |
| 1 | 3.886 | 0.067 | 0.026 |
| 2 | 2.919 | 0.110 | 0.041 |
| 3 | 2.334 | 0.218 | 0.110 |
| 4 | 1.631 | 0.169 | 0.046 |
| 5 | 1.921 | 0.139 | 0.195 |
| 6 | 0.948 | 0.186 | 0.149 |
| 7 | 3.496 | 0.173 | 0.063 |
| 8 | 2.097 | 0.228 | 0.093 |
| Mean | 2.404 | 0.161 | 0.090 |
| Duncan Test* | a | b | b |

EXAMPLE 5

Whole Peach Fruit Assay

Fresh, whole peaches were purchased at a local supermarket. Single fruits were placed into each of 24 one-quart jars and sealed with lids containing rubber septa. After two hours, headspace gas was sampled from each jar and ethylene content was determined by a gas chromatograph (Hewlett-Packard Model No. 5890) equipped with an FID. From the twenty-four fruit, fifteen fruit with the most uniform level of ethylene production were weighed and labeled. Into each treatment solution five of the fifteen fruit were submerged for fifteen minutes. Treatment solutions were as follows:

Solution #1 2.5 mM AVG+0.1% non-ionic surfactant
Solution #2 2.5 mM N-Acetyl AVG+0.1% non-ionic surfactant
Solution #3 Control (0.1% non-ionic surfactant only)

An organosilicone surfactant was used at 0.1 v/v in all treatments. Beginning twenty-four hours after treatment and continuing every twenty-four hours thereafter, the fruit were placed in one-quart jars for two to five hours and headspace samples were analyzed for ethylene as described above. Ethylene production was calculated on a nanoliter ethylene per gram fresh weight per hour basis. Negative values for "Days After Treatment" indicates the number of days prior to solution treatment.

TABLE 4

Ethylene Production from Peaches

| Days After Treatment | Solution 3 | Solution 2 | Solution 1 |
|---|---|---|---|
| -3 | 2.5 | 2.4 | 2.2 |
| 1 | 10 | 2.6 | 0.1 |
| 2 | 13.5 | 1.6 | 0.1 |
| 3 | 19.6 | 1.5 | 0.1 |

As shown by the data, N-acetyl AVG inhibits ethylene production in peach fruit.

EXAMPLE 6

Whole Apple Fruit Assay

Fresh, whole apples (cv. Granny Smith) were purchased at a local supermarket. Prior to experimentation each apple was washed with soapy water to remove surface residues. Single fruits were placed into each of 24 one-quart jars and sealed with lids containing septa. After two hours headspace gas was sampled from each jar and ethylene content was determined by a gas chromatogram (Hewlett-Packard Model No. 5890) equipped with an FID. From the twenty-four original fruit, fifteen fruit with the most uniform levels of ethylene production were weighed and labeled. Into each treatment solution listed in Example 5, five of the fifteen fruit were submerged for fifteen minutes. Beginning twenty-four hours after treatment and continuing every twenty-four hours thereafter, the fruit were placed in one-quart jars and sealed for two to five hours. Headspace samples were analyzed for ethylene as described above. In between headspace sampling periods, the jars were opened and the fruit were exposed to ambient conditions. Ethylene production was calculated on a nanoliter ethylene per gram fresh weight per hour basis. Negative values for "Days After Treatment" indicates the number of days prior to solution treatment.

TABLE 5

Ethylene Production from "Granny Smith" Apples

| Days After Treatment | Solution #3/Duncan Test | Solution #2 | Solution #1 |
|---|---|---|---|
| −3 | 23.1/ a | 25.8/ a | 23.4/ a |
| 1 | 26.8/ a | 25.2/ a | 9.8/ b |
| 2 | 31.5/ a | 20.3/ b | 8.4/ c |
| 3 | 36.9/ a | 20.2/ b | 8.1/ c |
| 4 | 39.3/ a | 18.5/ b | 7.4/ c |
| 8 | 39.3/ a | 13.1/ b | 8.2/ b |
| 16 | 37.6/ a | 9.7/ b | 10.8/ b |
| 22 | 30.6/ a | 10.3/ b | 10.7/ b |

The data were statistically analyzed using the Duncan Multiple Range Test as described in Example 3. As is shown from the data in Table 5, both N-acetyl AVG and AVG inhibit ethylene production in apples, with the efficiency of N-acetyl AVG and that of AVG being statistically indistinguishable after 8 days.

What is claimed is:

1. The compound L-trans-2-amino-4-(2-acetamidoethoxy)-3-butenoic acid, having the structure

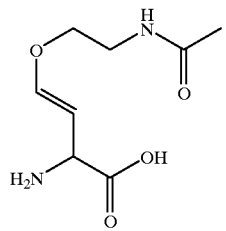

or an aliphatic or aromatic ester or salt thereof.

2. A composition comprising
   (a) the compound L-trans-2-amino-4-(2-acetamidoethoxy)-3-butenoic acid, or an aliphatic or aromatic ester or salt thereof and
   (b) an agronomically-acceptable carrier.

3. A composition comprising
   (a) the compound L-trans-2-amino-4-(2-acetamidoethoxy)-3-butenoic acid, or an aliphatic or aromatic ester or salt thereof,
   (b) one or more agronomically-acceptable adjuvants, and
   (c) an agronomically-acceptable carrier.

4. A composition of claim 2 wherein the agronomically-acceptable carrier is an aqueous carrier.

5. A composition of claim 4 wherein the aqueous carrier is water.

6. A composition of claim 3 wherein the agronomically-acceptable carrier is an aqueous carrier.

7. A composition of claim 6 wherein the aqueous carrier is water.

8. A composition of claim 3 wherein the agronomically-acceptable adjuvants comprise one or more adjuvants selected from the group consisting of preservatives, surfactants, wetting agents, emulsifying agents, and dispersing agents.

9. A composition of claim 8 wherein the adjuvants comprise a nonionic surfactant and optionally one or more adjuvants selected from the group consisting of preservative, wetting agents, emulsifying agents, and dispersing agents.

10. A method of inhibiting ethylene biosynthesis in a plant comprising administering to said plant an effective amount of a composition of claim 2.

11. A method of inhibiting ethylene biosynthesis in a plant comprising administering to said plant an effective amount of a composition of claim 3.

12. The method of claim 3 wherein said agronomically-acceptable carrier is an aqueous carrier.

13. A method of claim 12 wherein the aqueous carrier is water.

14. A method of claim 13 wherein said composition has from about 10 parts per million to about 2000 parts per million of said L-trans-2-amino-4-(2-acetamidoethoxy)-3-butenoic acid, or an aliphatic or aromatic ester or salt thereof.

15. A method of claim 14 wherein the composition further comprises between about 0.025% by weight to about 1% by weight of a nonionic surfactant.

16. A method of claim 11 wherein said composition is applied to at least one or more of leaves, buds, fruits, roots, stems, trunks, branches, or flowers of said plant.

17. A method of claim 16 wherein said composition is applied to at least one or more of said leaves or fruit of said plant.

18. A method of claim 16 wherein said composition is applied to at least one or more of said leaves, buds, or flowers of said plant.

* * * * *